United States Patent [19]
Gilchrist et al.

[11] Patent Number: 4,816,027
[45] Date of Patent: Mar. 28, 1989

[54] DISPOSABLE OSTOMY BAG LINER

[76] Inventors: Richard J. Gilchrist; Sarah J. Gilchrist, both of 6707 E. 99th St., South, Tulsa, Okla. 74133

[21] Appl. No.: 95,438

[22] Filed: Sep. 3, 1987

[51] Int. Cl.$^4$ ............................................. A61F 5/44
[52] U.S. Cl. ................................... 604/339; 604/332; 604/342
[58] Field of Search ............... 604/339, 338, 341, 342, 604/332, 333–335, 336, 337

[56] References Cited
U.S. PATENT DOCUMENTS

| | | | |
|---|---|---|---|
| 2,689,567 | 9/1954 | Welch | 604/333 |
| 3,089,493 | 5/1963 | Galindo | 604/342 |
| 3,419,913 | 1/1969 | Crosby | 4/144.2 |
| 4,256,110 | 3/1981 | Scoville | 604/342 |
| 4,460,363 | 7/1984 | Steer et al. | 604/336 |

Primary Examiner—Larry Jones
Attorney, Agent, or Firm—Richard C. Litman

[57] ABSTRACT

An ostomy replacement, disposable pouch liner that is enclosed by an ostomy pouch on which a locking ring, having a plurality of raised projections or ridges, mate or seal with a projection affixed to a flange appliance. A liner is disposed between said locking ring and said flange appliance projection and the liner is further disposed up around the periphery of said flange appliance such that the liner completely isolates and separates the ostomy pouch from the flange appliance, whereby the pouch is kept unspoiled and needs not be replaced as often, and the liner is easily disposed of.

2 Claims, 1 Drawing Sheet

DISPOSABLE OSTOMY BAG LINER

FIELD OF INVENTION

This invention relates to devices and methods for the hygienic replacement of ostomy liners.

BACKGROUND OF THE INVENTION

The present apparatus relates to replacement ostomy bags and more particularly to a device for the easy, convenient and expeditious replacement of the ostomy bag liner.

Specifically, this device relates to an improvement in ostomy bag liners such that the ostomy bag need not be replaced as often, because the liner is truly disposable.

This apparatus also relates to an improvement in the level of hygiene associated with the changing of a ostomy bag such that the device completely isolates and separates the liner from the ostomy bag, and further, provides a simplified method of disengaging the liner from the bag, keeping the contents of the liner isolated from the ostomy bag itself.

DESCRIPTION OF THE PRIOR ART

The following cited references are found to be exemplary of the prior U.S. art. They are:

| U.S. Pat. No. | Inventor |
| --- | --- |
| 2,741,247 | Marsan |
| 4,439,191 | Hogan |
| 3,089,493 | Galindo |

U.S. Pat. No. 2,741,247, issued to Marson, discloses an expendable colostomy or drainage pouch which is concerned with improvement in postoperative pouches.

U.S. Pat. No. 4,439,191, to Hogan, teaches a construction of an ostomy bag cover that is in the form of a hollow body and includes a first aperture formed therein to be disposed in registry with the inlet of the ostomy bag and to receive the connect member therethrough.

U.S. Pat. No. 3,089,493, issued to Galindo, discloses a colostomy bag with a disposable liner which can be worn at all times by the user.

SUMMARY OF THE INVENTION

A primary object of the present device is to provide a construction of an ostomy liner such that the liner completely isolates and separates the contents thereof with a ostomy pouch or bag.

Another object is to provide a liner configuration or construction that allows a truly disposable liner method or system of ostomy bag usage, such that the pouch or bag itself may be used for extended periods of time without the need for relatively expensive replacement.

A further object is to provide a construction for an ostomy liner system such that the elderly and visually impaired may use the system with confidence. The present apparatus or system giving them thereby convenience of use and savings in time, trouble and expense of maintaining the system.

DESCRIPTION OF THE PREFERRED EMBODIMENT

Figure 1:
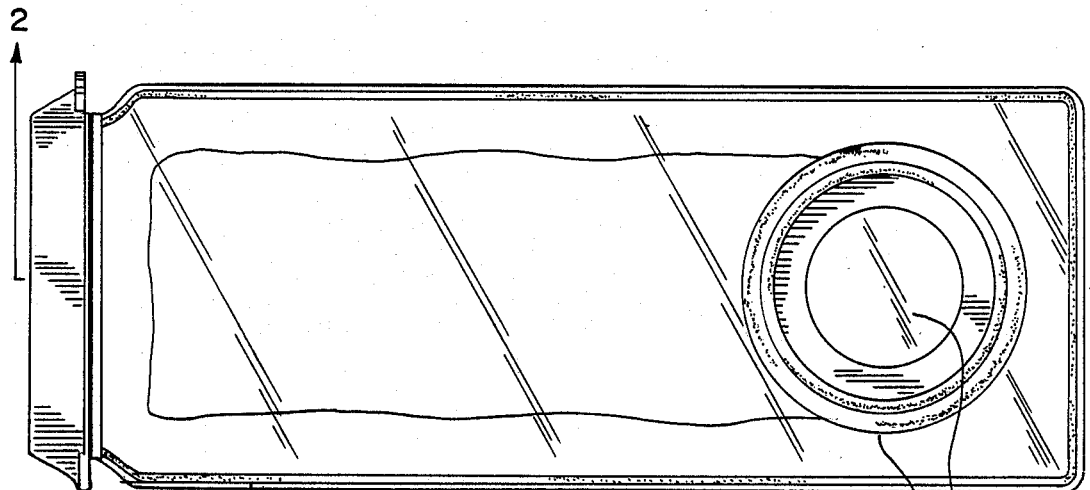
FIG. 1 is a front view of the device.
Figure 2:
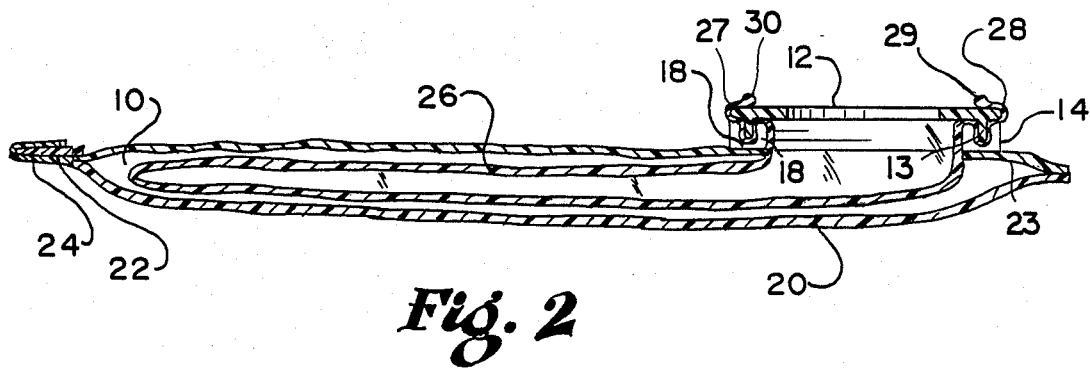
FIG. 2 is a section view through plane 2—2 of FIG. 1.
Figure 3:
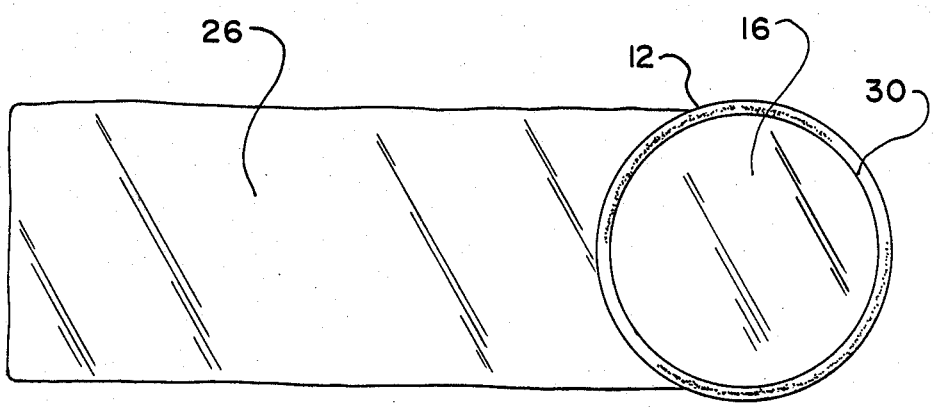
FIG. 3 is a front view of the liner as it encircles a body fitting flange.

Referring now to FIGS. 1 through 3, device 10 includes a apertured collar 12 that containing, on one side thereof, fastening means 14 that is a raised curvilinear projection.

Fastening means 14 extends around the periphery of apertured collar 12, the approximate center of which is proximate to an ostomy device worn by the patient or user.

The fastening or attachment element 14 will be seen to comprise a bifurcated member including a pair of concentric raised projections 18—18, curvilinear in configuration and axially extending from the fastening means 14 such that an axially disposed ring 13 extending from the collar 12 is seated or mated within the dual raised projections 18.

The fastening element 14 is affixed to an outermost ostomy pouch 20, which has drainage means 22 disposed at a terminal end thereof and closing or clamping means 24 for the temporary securing of drainage means 22. The other, open end 23 of the pouch is suitably affixed to the fastening element 14.

A replaceable liner 26 is enclosed within the ostomy bag or pouch 20 and includes a mouth opening 27 adapted to be securely sandwiched between the mating projections 18—18 and ring 13 such that a positive clamping or securing action is provided by the resilience of the materials, which may comprise VINYL or other composite materials. The mating of these components will be understood to hold or secure the liner 26 within the pouch 20.

The liner mouth edge 29 extends outward beyond the mating components and over the collar peripheral surface 28 such that the liner more fully envelopes the collar, thereby serving to completely isolate the pouch 20 from the collar exterior surface 28, so that the liner fully protects and separates the pouch. In this manner, the pouch remains clean and unsoiled when subsequently affixed to the user's body. The liner, of course, is disposable, as it is removably secured by the aforedescribed clamping action between the collar and fastening element.

Liner 26 is easy to remove as the user need only pull the pouch, with its affixed apertured collar, free of the fastening element 14 and this single action thereby also loosens liner 26 such that it can be lifted free and disposed of, or conversely, fastening means 14 can be loosened and liner 26 removed through the bottom of the pouch.

As elastic cuff 30 may be deployed around the exterior edges of flanged appliance such that the liner is further secured to the upper portion of apertured collar 12. The liner is then additionally sandwiched between the mating surfaces of fastening means 14 and collar 12.

It will be apparent that the objects and advantages of the present device have been disclosed and establishment, and further, since many small changes will occur to those skilled in the art, the foregoing is by way of illustration and examples of the principles of the invention. All equivalents thereof falling under the scope of the present invention. The limitations as such being determined only by the claims.

What is claimed is:
1. An ostomy device, comprising in combination:

an outer pouch having a substantially circular opening, a circular apertured fastener member affixed to said pouch adjacent said opening and having a pair of spaced apart concentric projections axially extending therefrom;

an apertured collar having attachment means comprising a curvilinear ring projection adapted to be inserted in a secure manner between said fastener member projections;

a disposable liner having a mouth opening and adapted to be inserted within said pouch with said liner extending through said fastener member and overlying said fastener member projections; said collar overlying said fastener member with said ring disposed between said spaced apart projections to securely clamp said liner relative said pouch opening; and said liner mouth opening bounded by an elastic member, whereby said elastic member maintains said liner mouth opening tightly disposed in a sealing engagement overlying said collar.

2. An ostomy device according to claim 1 including, closing and clamping means on said pouch at an end thereof opposite said pouch circular opening.

* * * * *